US008673827B1

(12) United States Patent
Hermes

(10) Patent No.: US 8,673,827 B1
(45) Date of Patent: Mar. 18, 2014

(54) METHOD OF ANALYSIS OF POLYMERIZABLE MONOMERIC SPECIES IN A COMPLEX MIXTURE

(75) Inventor: Robert E. Hermes, White Rock, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1561 days.

(21) Appl. No.: 11/998,331

(22) Filed: Nov. 28, 2007

(51) Int. Cl.
C09K 8/60 (2006.01)

(52) U.S. Cl.
USPC .......................................... 507/219; 507/266

(58) Field of Classification Search
USPC ....................................................... 507/219
See application file for complete search history.

(56) References Cited

U.S. PATENT DOCUMENTS

| 3,334,689 | A |   | 8/1967  | McLaughlin |         |
|-----------|---|---|---------|------------|---------|
| 3,370,009 | A | * | 2/1968  | Nolan, Jr. et al. | 508/223 |
| 3,490,533 | A |   | 1/1970  | McLaughlin |         |
| 5,335,726 | A |   | 8/1994  | Rodrigues  |         |
| 5,358,051 | A |   | 10/1994 | Rodrigues  |         |
| 6,187,839 | B1 |  | 2/2001  | Eoff et al. |        |
| 7,056,408 | B2 |  | 6/2006  | Whitman    |         |
| 2006/0054543 | A1 | | 3/2006 | Petro et al. |       |
| 2006/0269733 | A1 | | 11/2006 | Mizuno et al. |     |
| 2007/0114033 | A1 | | 5/2007 | Hermes et al. |      |
| 2007/0267193 | A1 | | 11/2007 | Hills et al. |       |

OTHER PUBLICATIONS

Index of Refraction of Organic Compounds; Robert C.Weast, Editor; CRC Handbook of Chemistry and Physics, 1st Student Edition, 1988; p. E-316.*
Gal et al, "The Detection and Determination of Ethyl and Methyl Alcohols in Mixtures by the Immersion Refractometer", J.A.C.S., vol. 27, (1905), pp. 964-972.
Herraez et al., "Refractive Indices, Densities, and Excess Molar Volumes of Monoalcohols + Water", J. Solution Chem. vol. 35, Sep. 2006, pp. 1315-1328.

* cited by examiner

Primary Examiner — John J Figueroa
Assistant Examiner — Atnaf Admasu
(74) Attorney, Agent, or Firm — Juliet A. Tanner

(57) ABSTRACT

Method of selective quantitation of a polymerizable monomeric species in a well spacer fluid, said method comprising the steps of adding at least one solvent having a refractive index of less than about 1.33 to a sample of the complex mixture to produce a solvent phase, and measuring the refractive index of the solvent phase.

26 Claims, 3 Drawing Sheets

US 8,673,827 B1

METHOD OF ANALYSIS OF POLYMERIZABLE MONOMERIC SPECIES IN A COMPLEX MIXTURE

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to a method of analysis of a polymerizable monomeric species in a complex mixture, for example well spacer fluid, by means of refractive index measurements.

BACKGROUND OF THE INVENTION

A major concern in drilling wells is that the lining of the shaft (the "casing") has the potential to collapse or rupture. When drilling a well, individual lengths of tubes often are secured together to form a casing string. Each section of the casing string may be cemented within the wellbore before a next smaller diameter portion is drilled and cased. The concentric casings form annuli which may or may not extend the full length of the well. Fluids, often referred to as spacer fluid or drilling fluid, typically are inserted between the top of the cement and the wellhead within the annular spaces. When these fluids are heated by oil pumped from deep within the ground and having a relatively high temperature, thermal expansion can create high pressures in the spacer fluid and result in collapse or rupture of the casing. This is commonly known as "annular pressure buildup." When this occurs, the well may become inoperable and another well must be drilled at a significant cost. In addition, contaminants may be leaked into the environment.

One solution to this problem is described in U.S. Patent Application 2007/0114033 (Hermes et al.), which describes a spacer fluid that decreases in volume as the temperature of the fluid is increased, thus reducing pressure build-up as high-temperature oil is pumped through the production tubing. The spacer fluid comprises a monomer which undergoes polymerization and decreases the volume of the fluid as the reaction proceeds. Just prior to inserting the spacer fluid into the well, the proper amount of initiator is added. Thus, it is of critical importance to know the amount of the monomer in the fluid, both at the time of mixing the fluid and prior to inserting the fluid into the well shaft.

Additionally, spacer fluids containing polymerizable monomers may be used for water control and/or shut-off applications in the drilling industry. During drilling, geological formations may be encountered which allow ingress of water (for example, underground aquifers) or egress of drilling fluid (for example, cavernous formations). In either case, the addition of spacer fluids containing polymerizable monomers can seal the geological formation when applied according to the teachings of U.S. Pat. No. 6,187,839. In these cases, it would also be important to know the amount of monomer in the fluid prior to application in the well.

Several factors complicate the determination of the amount of monomer in the fluid. First, the spacer fluid is a complex mixture that has a color and consistency similar to mud. Second, the spacer fluid may be prepared on land, and subsequently shipped by boat to an off-shore drilling rig, which may take several days and be subject to weather and/or drilling schedule delays. Thus, analysis may need to occur on the boat, which requires analytical instrumentation that is robust, compact (due to space constraints), accurate and relatively simple to use. A need exists, therefore, for a method of determining the concentration of a polymerizable monomeric species in well spacer fluid which meets the aforementioned criteria.

SUMMARY OF THE INVENTION

The present invention meets this need by providing a method for quantitation of a polymerizable monomeric species by use of a refractive index detector (refractometer). Refractometry instrumentation is robust, relatively straight-forward to use, and is available in a hand-held unit. One challenge in the application of refractometry as described herein, however, is finding a suitable solvent. The polymerizable monomeric species must be soluble in, and selectively partition into, the solvent. The remaining components of the complex mixture should be either insoluble in the solvent or, if soluble, should not appreciably contribute to a refractive index reading. In addition, the solvent must have a sufficiently low refractive index to provide maximum sensitivity, and must provide a sufficiently broad dynamic range. The latter is important when the spacer fluid is a shrinking spacer fluid, as a relatively large amount of the monomer may be required to sufficiently decrease the volume of the spacer fluid. Specifically, it has been found that the neat solvent should have a refractive index of 1.33 or lower. It has further been found that certain alcohol solvents meet the above criteria. It is further to be understood that the present invention may be applicable not only to well spacer fluid analysis, but to analysis of other complex mixtures that require quantitation of a monomeric species.

The following describe some non-limiting embodiments of the present invention.

In accordance with the purposes of the present invention is provided in one embodiment a method of selective quantitation of a polymerizable monomeric species in well spacer fluid, said method comprising adding at least one solvent having a refractive index of less than about 1.33 to a sample of the well spacer fluid to produce a solvent phase, and measuring the refractive index of the solvent phase.

A method of selective quantitation of a polymerizable monomeric species in well spacer fluid, said method comprising adding at least one solvent having a refractive index of less than about 1.33 to a first sample of the well spacer fluid to produce a first solvent phase; adding the same solvent to a second sample of the well spacer fluid to produce a second solvent phase; measuring a first refractive index of the first solvent phase at a first timepoint; measuring a second refractive index of the second sample at a second timepoint; using the first refractive index and the second refractive index to calculate a rate of polymerization of the monomeric species.

In yet another embodiment, a method of selective quantitation of a polymerizable acrylate monomer in a complex mixture comprising a polymer comprised of the acrylate monomer, comprising adding at least one solvent having a refractive index of less than about 1.33 to a sample of the complex mixture to produce a solvent phase, and measuring the refractive index of the solvent phase.

DETAILED DESCRIPTION OF THE INVENTION

Figure 1:
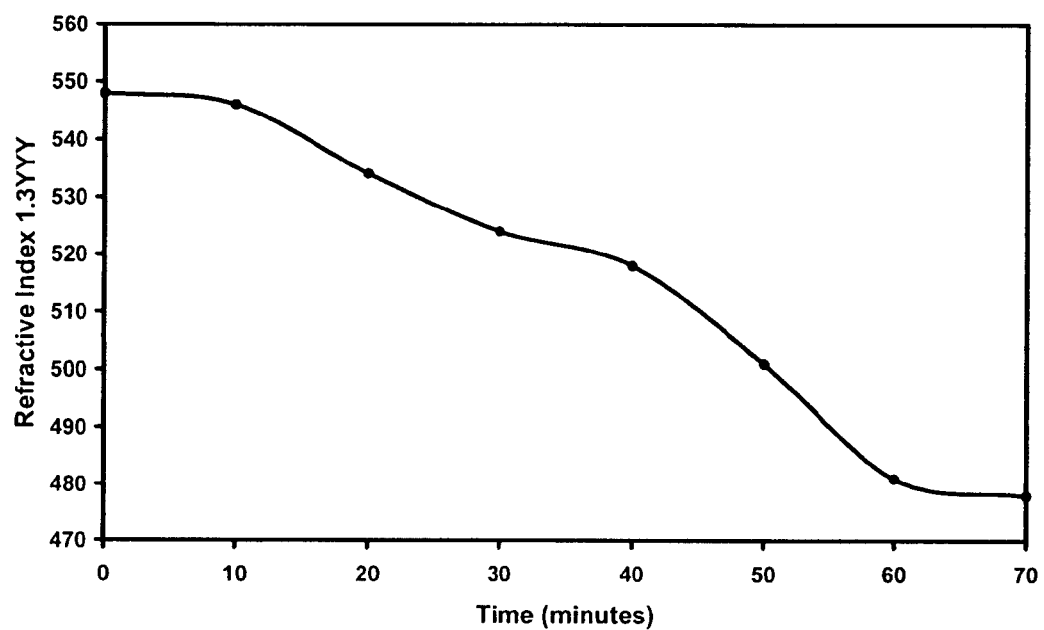
FIG. 1 depicts a graph of the concentration of methyl methacrylate in the solvent phase of a sample of shrinkable well spacer fluid. The y-axis represents the last 3 digits of the refractive index units (1.3YYY) and the x-axis depicts time during which the methyl methacrylate is depleted by polymerization.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

"Selective quantitation," as used herein, means determining the concentration of a polymerizable monomeric species absent significant interference from other species present in the sample.

"Polymerizable monomeric species," as used herein, means a chemical moiety capable of polymerization in the presence of a suitable initiator under suitable reaction conditions, as would be understood by one skilled in the art. Polymerization of a monomeric species is understood to result in a polymer comprised of the covalently bonded monomeric species.

"Well spacer fluid," as used herein, means a fluid suitable for use in a drilled well, and which may be in contact with the well casing, for example trapped in well casing annuli above the top-of-cement and below the wellhead. "Shrinking spacer fluid," as used herein, means a spacer fluid that decreases in volume upon reaction of chemical species present in the fluid, for example, a polymerization reaction.

"Water control fluid," as used herein, means a well spacer fluid suitable for use in a drilled well to plug geological spaces which either ingress water, or egress drilling fluid during the drilling process.

"Solvent phase" as used herein means the portion of the sample which comprises the bulk of a solvent and the species, dissolved therein, and which results from mixing the solvent with the sample and subsequently allowing the sample to partition into at least two physically discernable phases. For example, if methanol is added to a well spacer fluid, the solvent phase will comprise methanol and a relatively clear methanol-soluble fraction; measurement of the solvent phase by a refractometer will produce a resultant refractive index.

"Substantially insoluble," as used herein, means that a substance in a sample (e.g., well spacer fluid) substantially fails to partition into the solvent phase upon mixing with the sample. Any amount that may be soluble in the solvent is insufficient to significantly affect the quantitation of a polymerizable monomeric species in that solvent. In one embodiment, substantially insoluble means that at least 99% of the substance is insoluble in the solvent.

"Refractive Index," as used herein, means a refractive index measured according to the method described herein by means of a refractometer, one suitable example of which is a Palm Abbe™ digital refractometer, model PA202 or PA203, manufactured by Misco™, (Cleveland Ohio). The refractometer preferably has an accuracy and/or precision of about +/−0.0001 units and electronic temperature compensation capability.

Method

Figure 2:
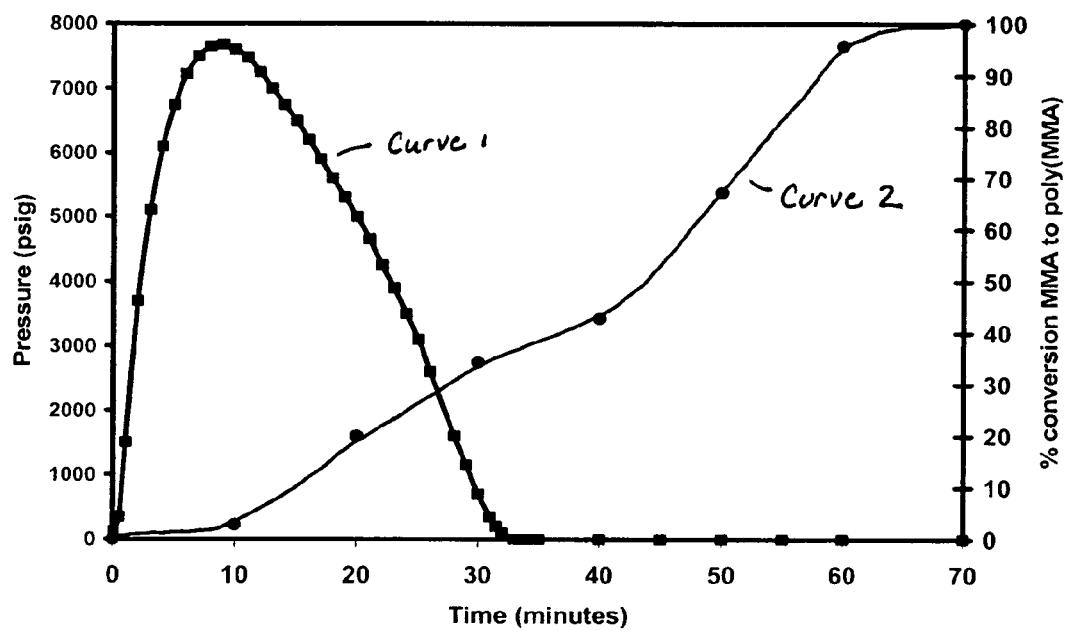
FIG. 2 depicts a graph of the change in concentration of methyl methylacrylate over time, where the primary y-axis (for curve 1) represents the pressure trace of the spacer fluid containing polymerizable monomer, the secondary y-axis (for curve 2) represents the percent conversion of methyl methacrylate monomer to polymer (calculated from the refractive index readings in FIG. 1), and the x-axis represents time in minutes.
Figure 3:
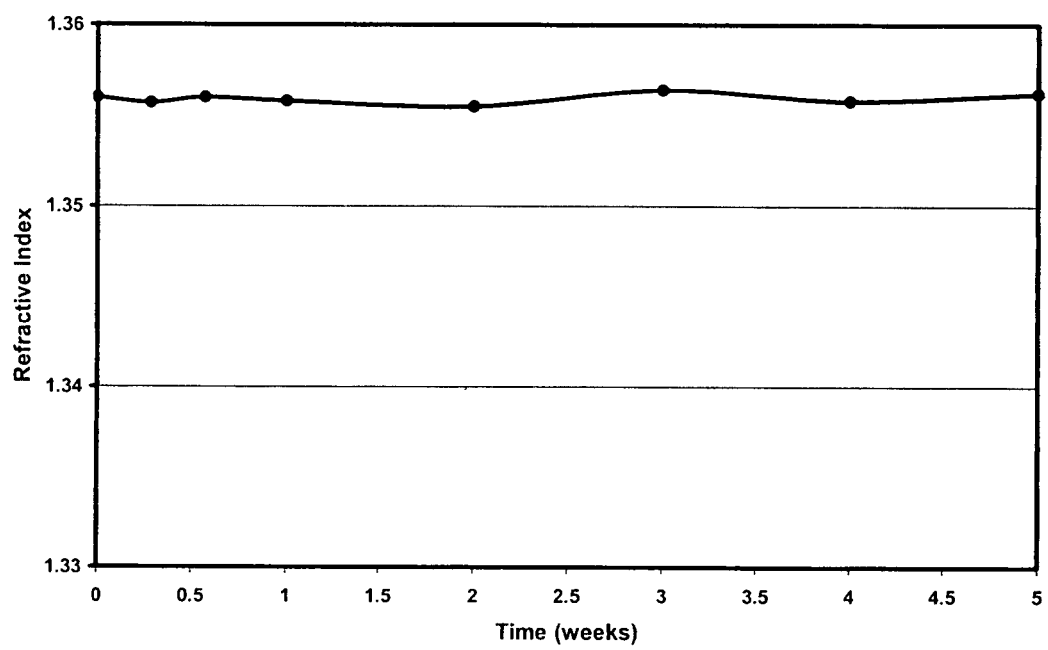
FIG. 3 depicts a graph of the stability of the methyl methacrylate polymerizable monomer in a spacer fluid containing a polymerization inhibitor as a function of time. The y-axis represents the refractive index, and the y-axis depicts time in weeks.

The method of the present invention comprises the step of adding at least one solvent as described herein to a sample of well spacer fluid to produce a solvent phase, and measuring the refractive index of the solvent phase. The sample may contain any amount suitable for measurement by a refractometer, but typically is on the order of 10.0 ml. The data obtained from the refractive index measurements may be used to quantitate the amount of a polymerizable monomeric species ("monomer") present in a sample, for example, by comparison to a calibration curve constructed from refractive index measurements of multiple samples containing known quantities of monomer. For example, a calibration curve may be constructed by plotting the refractive index obtained by measuring at least three refractive indices of at least three solvent phases comprising known amounts of monomer to produce a range of refractive indices, for example of from about 1.34 to at least 1.45. Alternatively, measurements of the refractive index of multiple samples held under the same thermal conditions may be made at given time intervals, the measurements converted to concentration of monomer or percent conversion to polymer, and plotted vs. time to produce information relating to the kinetics of the polymerization reaction (i.e., "kinetic data"). An example of kinetic data is depicted in FIG. 2, with additional information obtained from a pressure vessel experiment with the same formulation, that is, when shrinkage occurs within the vessel due to the polymerization of the methyl methacrylate monomer. Additionally, measurements of the refractive index of multiple samples held under the same thermal conditions may be made at given time intervals, and may provide information relating to the stability of the well spacer fluid (i.e., "stability data"). An example of stability data is depicted in FIG. 3.

In one non-limiting example, a chosen volume of polymerizable spacer fluid is added to a test tube and weighed. The same volume of a solvent is added, the test tube sealed with a screw cap, and shaken vigorously to mix the components. The spacer fluid components that do not dissolve in the solvent fraction settle out, usually within 5 minutes. The test tube is opened, and 2-3 drops are placed in the sample well of the portable refractometer. The refractive index reading is then compared to samples of known concentration, such as a calibration curve, a prepared spacer fluid at time zero, a percent conversion to polymer, or other convenient indicator of monomeric species left in the spacer fluid. The method is generally performed at a standard temperature of about 20° C.

Refractometer

For the purposes of the present invention, any instrument capable of measuring the refractive index of a liquid sample may be used. The instrument may be the size of a benchtop model, a handheld model, or of a size therebetween. In one embodiment, the refractometer is a hand-held refractometer. In one embodiment, the refractometer is capable of measuring refractive indices of from at least 1.3 to about 1.5, and more preferably from about 1.3330 to about 1.5040. One example of a commercially available refractometer suitable for this purpose is a MISCO™ Model PA202 Palm Abbe™ Digital Refractometer, calibrated and used in accordance with the original instructions.

Solvent

For the purposes of the present invention, "solvent" is understood to mean a single solvent or a mixture of two or more solvents wherein the solvent or mixture of solvents has a refractive index which is less than purified water. In other words, when two or more solvents are present, an individual solvent may have a refractive index of greater than that of purified water, however, if the refractive index of the combination of solvents is less than that of purified water, then the combination is considered a suitable solvent for the purposes of the present invention. It is further known that mixtures of alcohols and water produce higher refractive indices than either of the two neat liquids alone, as discussed in A. E. Leach and H. C. Lythgoe, "The detection and determination of ethyl and methyl alcohols in mixtures by the immersion refractometer", J.A.C.S. 27, 964 (1905), and J. V. Herraez and R. Belda, "Refractive indices, densities, and excess molar volumes of monoalcohols+water", J. Solution Chem. 35, 1315 (2006). Both references note that when methanol is present in the mixture, the refractive index is raised to a lesser degree than other alcohols (for example, water has a refractive index of 1.3326, and methanol has a refractive index of 1.3264, whereas a 0.333 mixture (by mole fraction) of the two produces a refractive index of 1.3396. Thus, methanol would provide a larger dynamic range for the determination of polymerizable monomeric species in the spacer fluid composition.

In one embodiment, the refractive index the solvent is about 1.4 or less, alternatively is about 1.34 or less, and alternatively is from about 1.32 to about 1.34. The solvent should be immiscible in the well spacer fluid, i.e. when mixed with the well spacer fluid and allowed to stand for a period of time, the solvent should form a separated solvent phase that is distinguishable on the basis of color, opacity, or other physical criteria. The polymerizable monomeric species should be substantially soluble in the solvent, whereas the corresponding polymer should be substantially insoluble. Preferably, the components of the well spacer fluid, other than the polymerizable monomeric species, also are substantially insoluble in the solvent, or if soluble, do not substantially interfere with refractive index measurements.

In one embodiment, the solvent is a simple alcohol, understood herein to mean a $C_1$-$C_4$ alcohol, for example, methanol, ethanol, propanol, butanol, and combinations thereof. In an alternative embodiment, the solvent is methanol. In yet another embodiment, the solvent is substantially free of methanol.

Well Spacer Fluid

The well spacer fluid may be any fluid comprising a polymerizable monomeric species that is inserted into a drilled well shaft, for example an oil well shaft, and which may be placed in contact with the well casing or with a geological formation. In one embodiment the well spacer fluid is a shrinkable well spacer fluid. In an alternative embodiment, the well spacer fluid is a water control fluid. One example of a shrinkable well spacer fluid is described in U.S. Patent Application 2007/0114033 (Hermes et al.). The well spacer fluid is a complex mixture that may comprise a plurality of components, including but not limited to water, a thickening agent (or "viscosifier"), barite, emulsifiers, defoamer, polymerization inhibitor, polymerization initiator, a base, a dispersant, the polymerized monomeric species (i.e., the "corresponding" polymer of the polymerizable species), and combinations thereof. In one embodiment, the well spacer fluid comprises an additional component selected from the group consisting of an initiator, an inhibitor, an emulsifier, a viscosifier, a weighting agent, and combinations thereof. The additional components preferably are insoluble in the added solvent and do not significantly partition into the solvent upon mixing with the sample. To the extent that an additional component is soluble in the added solvent, the component should interfere minimally with the determination of the refractive index. Preferably, any interference with the refractive index determination would produce a change in refractive index that is within the margin of error of the instrument.

Polymerizable Monomeric Species

The polymerizable monomeric species may be any species suitable for use in well spacer fluid and capable of undergoing polymerization under suitable reaction conditions. The monomer should be substantially soluble in the solvent which is added to the well spacer fluid and should produce a detectable difference in the refractive index when present in the solvent. One preferred class of polymerizable monomeric species suitable for use in the present invention is acrylate polymerizable monomers, understood herein to include acrylate- and methacrylate-containing monomers. Non-limiting examples of suitable polymerizable monomeric species include, but are not limited to, methyl acrylate, methyl methacrylate, methacrylic acid, acrylamide, N-methyl acrylamide, N-methyl methacrylamide, N,N-dimethyl acrylamide, N,N-dimethyl methacrylamide, ethyl acrylate, ethyl methacrylate, N-ethyl acrylamide, N-ethyl methacrylamide, N,N-diethyl acrylamide, N,N-diethyl methacrylamide, N,N-diethylaminoethyl acrylate, N,N-diethylaminoethyl methacrylate, 2-methoxyethyl acrylate, 2-methoxyethyl methacrylate, N-(2-methoxyethyl)acrylamide, N-(2-methoxyethyl)methacrylamide, n-propyl acrylate, 2-propyl acrylate, n-propyl methacrylate, 2-propyl methacrylate, N-(n-propyl)acrylamide, N-(n-propyl)methacrylamide, N-(2-propyl)acrylamide, N-(2-propyl)methacrylamide, n-butyl acrylate, n-butyl methacrylate, N-(n-butyl)acrylamide, N-(n-butyl methacrylamide), ethoxyethyl acrylate, ethoxyethyl methacrylate, N-(ethoxyethyl)acrylamide, N-(ethoxyethyl methacrylamide), 4-ethoxyethyl styrene, ethoxyethoxyethyl acrylate, ethoxyethoxyethyl methacrylate, N-ethoxyethoxyethyl acrylamide, N-ethoxyethoxyethyl methacrylamide, glycidyl acrylate, glycidyl methacrylate, N-(glycidyl)acrylamide, N-glycidyl methacrylamide, hexoxyethyl acrylate, hexoxyethyl methacrylate, 2-hydroxyethyl acrylate, 2-hydroxyethyl methacrylate, N-(2-hydroxyethyl acrylamide), N-(2-hydroxyethyl methacrylamide), 2-hydroxypropyl acrylate, 2-hydroxypropyl methacrylate, N-(2-hydroxypropyl acrylamide), N-(2-hydroxypropyl methacrylamide), polyethylene glycol monoacrylate, polyethylene glycol monomethacrylate, N-(polyethylene glycol)monoacrylamide, N-(polyethylene glycol)monomethacrylamide, methyl ether polyethylene glycol monoacrylate, methyl ether polyethylene glycol monomethacrylate, methyl ether N-(polyethylene glycol)monoacrylamide, methyl ether N-(polyethylene glycol)monomethacrylamide, polyethylene glycol diacrylate, polyethylene glycol dimethacrylate, N,N-(polyethylene glycol)diacrylamide, N,N-(polyethylene glycol)dimethacrylamide, 4-vinyl pyridine, N-vinyl pyrrolidone, cyanoethyl acrylate, cyanoethyl methacrylate, ethoxytriethylene glycol acrylate, ethoxytriethylene glycol methacrylate, N-(ethoxytriethylene glycol) acrylamide, N-(ethoxytriethylene glycol) methacrylamide, N,N-methylenebis acrylamide, N,N-methylenebis methacrylamide, vinyl acetate, vinyl chloride, vinyl acrylate, vinyl methacrylate, vinyl azlactone, acrylonitrile, 2-acetamidoacrylic acid, methyl 2-acrylamido-2-methoxyacetate, styrene, benzyl acrylate, benzyl methacrylate, N-(benzyl)acrylamide, N-(benzyl)methacrylamide, cyclohexyl acrylate, cylcohexyl methacrylate, N-(cyclohexyl)acrylamide, N-(cyclohexyl)methacrylamide, and N-butylurethane-O-ethyl acrylate (commercially available as CL-1039). In one embodiment, the polymerizable monomeric species is selected from the group consisting of methyl acrylate, methyl methacrylate, methacrylic acid, acrylamide, n-vinyl pyrrolidone, N-butylurethane-O-ethyl acrylate, methyl ether polyethylene glycol monomethacrylate, 2-hydroxyethyl methacrylate, and mixtures thereof.

The present invention is more particularly described in the following examples that are intended as illustrative only, as numerous modifications and variations will be apparent to those skilled in the art.

EXAMPLES

Example 1

A 12.8 pounds per gallon (ppg) water based spacer fluid containing methyl methacrylate at a predetermined concentration was obtained. A portion of the fluid was placed within a pressure vessel containing a standard pressure gauge, and heated in a boiling water bath. Pressure developed within until polymerization proceeds to a sufficient level to start decreasing the pressure due to shrinkage during the polymerization process. In addition, several test tubes were charged with 10.0 mL (15.4 grams) of the same fluid, and placed into a boiling water bath. At selected intervals, a test tube was removed and quenched in an ice water bath. Methyl alcohol (10.0 mL) was added, with the test tube shaken for about 15 seconds to afford complete mixing. Within about 5 minutes, the solids settled out, leaving a clear to slightly opaque supernatant on top. Centrifugation, although possible, was found to be unnecessary. The supernatant contained methyl alcohol, water, surfactant, and monomer. Two to three drops were analyzed using the portable refractometer. For convenience, the last three digits of the refractive index (1.3 YYY) were used for the graphical representation depicted in FIG. 1. FIG. 2 shows the data after mathematically converting the refractive index measurements to percent conversion of methyl methacrylate to poly(methyl methacrylate), and includes the pressure trace obtained from the pressure vessel as well. This composite graph clearly shows that at about 38% conversion, the pressure in the vessel has been totally compensated for by the shrinkage obtained during polymerization.

Example 2

An 11.0 pounds per gallon (ppg) water based spacer fluid containing methyl methacrylate at a predetermined concentration was obtained. Several test tubes were charged with 10.0 mL (13.2 grams), capped, and placed into a constant temperature water bath at 50° C. At selected intervals, a test tube was removed and quenched in an ice water bath. Methyl alcohol (10.0 mL) was added, with the test tube shaken for about 15 seconds to afford complete mixing. Within about 5 minutes, the solids settled out, leaving a clear to slightly opaque supernatant on top. Centrifugation, although possible, was found to be unnecessary. The supernatant contained methyl alcohol, water, surfactant, and monomer. Two to three drops were analyzed using the portable refractometer. The amount of the methyl methacrylate in the spacer fluid over a five week period at elevated temperature was shown to be very stable, as shown in FIG. 3. This graph also demonstrates the practical accuracy of the method, that is, readings are consistent within about +/−0.0003.

Example 3

The monomers listed in Table 1 were analyzed in a method similar to Example 2: eleven parts (by weight) of the water based spacer fluid was added to a sufficient number of test tubes to test the monomers in Table 1 in duplicate. Two parts of the appropriate monomer was added, with the addition of an azo-type free radical initiator solution in water (0.4 parts of a 25 wt. % solution). A duplicate set of blank control test tubes without monomer was prepared. Each tube was shaken to dissolve and/or evenly distribute the monomer within the spacer fluid. The first tube in each series was not heated, but immediately treated with 10 mL methanol (no polymerization), and shaken to afford complete mixing. The second tube in each series was heated in a boiling water bath for 90 minutes, and, for the purposes of this invention, was assumed to have complete polymerization. After quenching in an ice water bath, each tube was treated with 10 mL methanol as before. The contents generally settled out to form two layers, one barite rich layer, and one supernatant containing the methanol soluble fraction. Analysis with the refractometer provided refractive indices (R.I.) of the monomeric methanolic supernatant (first tube in each series), and the refractive indices of the polymerized methanolic supernatant (second tube in each series). The data clearly indicates the utility of the invention as shown by the last column (the "dynamic range").

| Monomer | First Tube R.I. | Second Tube R.I. | R.I. difference (range - three digits) |
|---|---|---|---|
| Methyl methacrylate | 1.3557 | 1.3470 | 0.0087 (87) |
| Methyl acrylate | 1.3545 | 1.3484 | 0.0061 (61) |
| Methacrylic acid | 1.3576 | 1.3572 | 0.0004 (4) |
| N-vinylpyrrolidone | 1.3648 | 1.3620 | 0.0028 (28) |
| N-butylurethane-O-ethyl acrylate | 1.3591 | 1.3480 | 0.0111 (111) |
| methyl ether polyethylene glycol monomethacrylate | 1.3597 | 1.3504 | 0.0093 (93) |
| 2-hydroxyethyl methacrylate | 1.3579 | 1.3496 | 0.0083 (83) |
| acrylamide | 1.3610 | 1.3479 | 0.0131 (131) |
| Control (no monomer) | 1.3477 | 1.3477 | 0.0000 (0) |

The method in Example 2 to convert last three digits of refractive index to % conversion to monomer:

$$100(\%)/\text{original refractive index−final refractive index} = \% \text{ per R.I. unit} \quad (1)$$

$$(\text{original refractive index−"found" refractive index at time increment}) \times (\% \text{ per R.I. unit}) = \% \text{ conversion of monomer to polymer} \quad (2)$$

For example: 100/548−478=1.428, then at the 40 minute value of 518 the result is (548−518)×1.428=42.8% conversion of monomer to polymer

What is claimed is:

1. A method of selective quantitation of a polymerizable monomeric species in well spacer fluid, said method comprising adding at least one solvent having a refractive index of less than about 1.33 to a sample of the well spacer fluid to produce a solvent phase, measuring the refractive index of the solvent phase, and thereafter using the well spacer fluid with a drilled well.

2. The method of claim 1, wherein the solvent is a simple alcohol.

3. The method of claim 2, wherein the simple alcohol is methanol.

4. The method of claim 1, wherein the solvent is substantially free of methanol.

5. The method of claim 1, wherein the polymerizable monomeric species is an acrylate monomer.

6. The method of claim 1, wherein the polymerizable monomeric species is selected from the group consisting of methyl acrylate, methyl methacrylate, methacrylic acid, acrylamide, n-vinyl pyrrolidone, N-butylurethane-O-ethyl acrylate, methyl ether polyethylene glycol monomethacrylate, 2-hydroxyethyl methacrylate, styrene, and mixtures thereof.

7. The method of claim 6, wherein the polymerizable monomeric species is methyl methacrylate.

8. The method of claim 1 wherein the well spacer fluid further comprises a polymer comprised of the polymerizable monomeric species, wherein said polymer is substantially insoluble in the solvent phase.

9. The method of claim 8, wherein the polymer is selected from the group consisting of poly(methylmethacrylate), poly(methacrylic acid), polystyrene, and mixtures thereof.

10. The method of claim 9, wherein the polymer is poly(methylmethacrylate).

11. The method of claim 1 wherein the well spacer fluid is a shrinking spacer fluid comprising at least one additional component selected from the group consisting of an initiator, an inhibitor, an emulsifier, a viscosifier, a weighing agent, and combinations thereof.

12. The method of claim 1, wherein the well spacer fluid is a water control fluid.

13. The method of claim 1, wherein the refractive index of the solvent phase is from about 1.33 to about 1.43.

14. The method of claim 1, wherein the refractive index is measured by means of a handheld refractometer.

15. A method of selective quantitation of a polymerizable monomeric species in well spacer fluid, said method comprising
 a) adding at least one solvent having a refractive index of less than about 1.33 to a first sample of the well spacer fluid to produce a first solvent phase;
 b) adding the same solvent to a second sample of the well spacer fluid to produce a second solvent phase;
 c) measuring a first refractive index of the first solvent phase at a first timepoint;
 d) measuring a second refractive index of the second sample at a second timepoint;
 e) using the first refractive index and the second refractive index to calculate a rate of polymerization of the monomeric species, and thereafter
 f) using the well spacer fluid with a drilled well.

16. The method of claim 15, wherein the solvent comprises methanol.

17. The method of claim 15, wherein the polymerizable monomeric species is methyl methacrylate.

18. A method of selective quantitation of a polymerizable acrylate monomer in a complex mixture comprising a polymer comprised of the acrylate monomer, comprising adding at least one solvent having a refractive index of less than about 1.33 to a sample of the complex mixture to produce a solvent phase, measuring the refractive index of the solvent phase, and thereafter using the well spacer fluid with a drilled well.

19. The method of claim 18, wherein the complex mixture is well spacer fluid, a water control fluid, or a combination thereof.

20. The method of claim 18, wherein the solvent comprises methanol.

21. The method of claim 1, wherein the step of using the well spacer fluid with a drilled well comprises inserting the well spacer fluid into a well shaft.

22. The method of claim 1, wherein the step of using the well spacer fluid with a drilled well comprises trapping the well spacer fluid in well casing below a well head.

23. The method of claim 15, wherein the step of using the well spacer fluid with a drilled well comprises inserting the well spacer fluid into a well shaft.

24. The method of claim 15, wherein the step of using the well spacer fluid with a drilled well comprises trapping the well spacer fluid in well casing below a well head.

25. The method of claim 18, wherein the step of using the well spacer fluid with a drilled well comprises inserting the well spacer fluid into a well shaft.

26. The method of claim 18, wherein the step of using the well spacer fluid with a drilled well comprises trapping the well spacer fluid in well casing below a well head.

\* \* \* \* \*